US012759993B2

(12) United States Patent
Xiong et al.

(10) Patent No.: US 12,759,993 B2
(45) Date of Patent: Oct. 13, 2026

(54) PROCESS FOR REFINING GLYCOLIDE AND GLYCOLIDE OBTAINED THEREFROM

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Wentao Xiong, Shanghai (CN); Rui Wang, Shanghai (CN); Fen Zhou, Shanghai (CN); Jingen Xiong, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 661 days.

(21) Appl. No.: 18/250,516

(22) PCT Filed: Oct. 26, 2021

(86) PCT No.: PCT/CN2021/126351
§ 371 (c)(1),
(2) Date: Apr. 25, 2023

(87) PCT Pub. No.: WO2022/089413
PCT Pub. Date: May 5, 2022

(65) Prior Publication Data

US 2023/0416220 A1 Dec. 28, 2023

(30) Foreign Application Priority Data

Oct. 26, 2020 (CN) ........................ 202011155982.3

(51) Int. Cl.
*C07D 319/12* (2006.01)

(52) U.S. Cl.
CPC .................................. *C07D 319/12* (2013.01)

(58) Field of Classification Search
None
See application file for complete search history.

(56) References Cited

U.S. PATENT DOCUMENTS

| | | | | |
|---|---|---|---|---|
| 5,223,630 | A | 6/1993 | Lin | |
| 5,830,991 | A * | 11/1998 | Shiiki | C07D 319/12 528/495 |
| 2003/0191326 | A1* | 10/2003 | Yamane | C07D 319/12 549/267 |
| 2012/0289713 | A1 | 11/2012 | Suzuki et al. | |
| 2015/0259320 | A1 | 9/2015 | Ohzawa et al. | |

FOREIGN PATENT DOCUMENTS

| | | | | |
|---|---|---|---|---|
| CN | 100999516 | | * | 7/2007 |
| CN | 100999516 | A | | 7/2007 |
| CN | 101054371 | A | | 10/2007 |
| CN | 102712617 | A | | 10/2012 |
| CN | 105272958 | A | | 1/2016 |
| CN | 107868074 | A | | 4/2018 |
| CN | 107868075 | A | * | 4/2018 |
| JP | 2002128777 | A | * | 5/2002 |

OTHER PUBLICATIONS

Wu, Qing-Yun et al.; "Synthesis of Glycolide"; Fine Chemicals; vol. 29, No. 4; Apr. 30, 2012; pp. 413-416.
Xiao, Tianpengfei et al.; "Technology Progress of Glycolide Synthesis"; China Science and Technology Information; vol. 13; Jul. 31, 2013; pp. 124.

* cited by examiner

*Primary Examiner* — Valerie Rodriguez-Garcia
(74) *Attorney, Agent, or Firm* — NKL Law; Allen Xue

(57) ABSTRACT

A process for refining glycolide includes a step of extracting impurities from a crude glycolide with solvent A, and then a step of recrystallizing with solvent B. Solvent A includes at least two solvents and the solvents are miscible each other. In the process, two types of polar solvents are used for the refining of crude glycolide. The process has a good extraction effect on acidic impurities such as glycolic acid oligomers. The solvents are easily fully removed during the solid-liquid separation and the drying process. Glycolide obtained using this process may have a low free acid content.

10 Claims, No Drawings

PROCESS FOR REFINING GLYCOLIDE AND GLYCOLIDE OBTAINED THEREFROM

TECHNICAL FIELD

The present invention relates to the field of glycolide, in particular to a process for refining glycolide and the glycolide obtained therefrom.

BACKGROUND TECHNOLOGY

Polyglycolic acid (PGA) is a synthetic polymer material with good biodegradability and biocompatibility. Unlike the traditional polymer materials with stable performance, such as plastics and rubber, after PGA is used as a material for a certain period of time, it will gradually degrade and finally turn into water and carbon dioxide that are harmless to the human body, animals, plants and the natural environment. The application of polyglycolic acid is mainly manifested in two aspects of biomedicine and ecology.

Glycolide is a cyclic dimer of glycolic acid, that is, a cyclic substance formed by the dehydration and condensation of two molecules of glycolic acid. The ring-opening polymerization of glycolide is a relatively mature process for preparing polyglycolic acid, which can obtain polyglycolic acid products with higher relative molecular weight. At present, the most mature and widely used synthetic process of glycolide at home and abroad is mainly the poly-condensation-depolymerization process of glycolic acid as raw material.

CN105272958A discloses a process for preparing glycolide, which is an example of using poly-condensation-depolymerization process to prepare crude glycolide. Firstly, under atmospheric pressure, glycolic acid is gradually heated to a maximum temperature of 200° C. for the poly-condensation reaction and the water generated in the reaction is removed. After the water output reaches a certain level, the water is further removed under reduced pressure to obtain a poly-condensation product with a higher molecular weight. Then under an ultra-high vacuum with the vacuum degree of 0.1-1 kPa, the glycolic acid pre-polymer and stannous octoate (the trans-esterification catalyst, which is added before the pre-polymerization) are heated to a temperature between 230° C. and 290° C. The glycolide vapor generated in the reaction is collected, and cooled to produce the crude product as a yellow solid.

The crude glycolide obtained from the above-mentioned depolymerization reaction usually contains various impurity such as water, glycolic acid, glycolic acid oligomer (having a molecular weight of lower than 500 g/mol), polyglycolic acid (having a molecular weight of higher than 500 g/mol). The existence of a very small amount of active hydrogen in the ring-opening polymerization of lactides will have a great impact on the molecular weight of the obtained polymer. Polyglycolic acid that needs to meet the requirements of surgical sutures and the like needs to meet the intrinsic viscosity of greater than or equal to 1, and the weight-average molecular weight of greater than 100,000. Therefore, crude glycolide needs to be refined to remove impurities as much as possible to obtain high-purity glycolide products.

In addition, it is worth noting that due to the use of solvents in the process of preparing refined glycolide from crude glycolide, a trace amount of solvent molecules are inevitably introduced into the glycolide product, and the solvent molecules are likely to contain active hydrogen, which will produce an adverse impact on the polymerization reaction of glycolide. During the polymerization process of glycolide, a part of the trace amount of solvent molecules will remain in PGA, which affects the biomedical application of PGA in the human body. Therefore, it is very important to use a suitable process to solve the problem of solvent residue in refined products.

The existing glycolide refining technology mainly includes recrystallization process (cooling recrystallization and evaporation recrystallization), alcohol washing process and the like. Among them, the process of recrystallization is the most used, and it is more common to use ethyl acetate as a representative organic solvent to recrystallize the crude glycolide repeatedly. Since these organic solvents are suitable solvents for glycolide, which has a high affinity at the molecular level with suitable solvents, it is difficult to entirely remove the solvents in the refined glycolide after drying. For example, the residual ethyl acetate content after sufficient drying can reach 500 ppm or higher, which causes ethyl acetate to still remain in the polymer PGA after the polymerization reaction.

Besides the technical solution of multiple recrystallizations with ethyl acetate to refine the glycolide, the prior art also includes such a technical solution, in which the coupling of recrystallization and alcohol washing refines the glycolide. For example, patent CN107868075A discloses a process for refining the glycolide, in which the crude glycolide is purified with a technical solution including cooling recrystallization, mixing with poor solvent, washing, filtering, and drying. Since during the final drying, the residual solvent in the glycolide becomes alcohol that is regarded as a poor solvent for the glycolide, this technical solution can also fully reduce the solvent residue, but in the process of mixing and washing with the poor solvent, the impurities adsorbed on the surface of the glycolide crystal particles are mainly removed, but the impurity crystal nucleus embedded in the crystals can hardly be removed, which causes that the effect of mixing and washing on the purification of impurities is not as good as that of recrystallization, making it difficult to reduce the terminal carboxyl content in the finally obtained refined glycolide product to $1.0\times10^{-5}$ mol/g or lower. Moreover, when the quality of crude glycolide is not good, for example, the crude glycolide purity is lower than 85% or the terminal carboxyl content is greater than $5.2\times10^{-4}$ mol/g, purifying the crude glycolide by only using an alcohol compound does not bring a good effect.

SUMMARY OF THE INVENTION

The technical problem to be solved by the present invention is the problem that the residual amount of solvent in the refined glycolide obtained by the existing crude glycolide purification process is relatively high, and the present invention provides a refining technical solution different from the technical solution of the coupling of recrystallization and washing, which has the technical advantages such as easy solvent recovery and low free acid content in the product.

One of the objects of the present invention is to provide a process for refining glycolide, which comprises a step of extracting impurities from a crude glycolide with solvent A, and then a step of recrystallizing with solvent B, wherein solvent A includes at least two solvents and the solvents are miscible each other. By adjusting the recrystallization-washing coupling order in the prior art, the impurities enwrapped by the recrystallization are significantly reduced, and a better overall refining effect is achieved.

Preferably, the process for refining glycolide comprises the following steps:

(1) mixing and stirring a crude glycolide and solvent A, then filtering the resulting solid-liquid mixture, and collecting the resulting filter cake;

(2) mixing the filter cake obtained in step (1) with solvent B, heating the resulting mixture, then cooling the resulting solution so as to separate out glycolide crystals, and collecting the resulting filter cake by filtering;

preferably, vacuum drying the obtained filter cake after repeating the step (2) at least once, so as to produce the refined glycolide.

In step (1), the temperature for mixing is 0-40° C., preferably 0-20° C.

In step (2), the temperature to which the resulting mixture is heated is 70-80° C., preferably 75-80° C.; the temperature to which the resulting solution is cooled is 0-25° C., preferably 15-25° C.

According to a preferred embodiment of the present invention, the process for refining crude glycolide comprises: (1) mixing and stirring a crude glycolide and solvent A, then filtering the resulting solid-liquid mixture, and collecting the resulting filter cake; (2) dissolving the filter cake obtained in step (1) in solvent B at a constant temperature of 70-80° C., cooling the resulting solution to 0-25° C. so as to separate out glycolide crystals, and collecting the resulting filter cake by filtering; (3) vacuum drying the obtained filter cake after repeating the step (2) at least once, so as to produce the refined glycolide product.

In any of the above technical solutions, said solvent A is a mixed solvent of solvent I and solvent II, solvent I is selected from polyalcohol ethers having the boiling point under atmospheric pressure of greater than or equal to 180° C., solvent II is selected from saturated alcohols having the boiling point under atmospheric pressure of less than or equal to 120° C.; solvent I is preferably selected from at least one of polyalkylene glycol ethers, solvent II is preferably selected from at least one of saturated monohydric alcohols.

Said solvent B is selected from saturated alcohols having the boiling point under atmospheric pressure of less than or equal to 120° C., preferably selected from at least one of saturated monohydric alcohols, said solvent B and solvent II can be identical or difficult.

In any of the above technical solutions, said solvent I, solvent II and solvent B are all polar solvents, and are subjected to the technologies such as azeotropic dehydration or molecular sieve adsorption dehydration before contacting the crude glycolide so as to have a water content of below 40 ppm.

In any of the above technical solutions, said solvent A is a homogeneous liquid at normal temperature, and the components therein are miscible, and the mass fraction of solvent II in solvent A is greater than or equal to 50%, and not equal to 100%; preferably 50-80%, that is, the proportion of solvent I with a higher boiling point in solvent A is limited. This is not only to ensure that solvent I all enters the liquid phase through several solid-liquid separation processes and does not remain in the glycolide, but also to prevent the glycolide from being dissolved in the solvent as the used amount of solvent I increases, resulting in an unacceptable loss of the refining yield.

In any of the above technical solutions, said solvent I is selected from at least one of polyalkylene glycol monoethers or polyalkylene glycol diethers; from the perspective of easy access to raw materials and easy synthesis, polyethylene glycol ethers are preferred; considering the solubility of solvent I in saturated monohydric alcohols and its fluidity, polyethylene glycol diether is preferred as polyethylene glycol ethers, and the polymerization degree of ethylene glycol in polyethylene glycol diether is preferably less than or equal to 20, more preferably less than or equal to 10; the ether groups at both ends of polyethylene glycol diether are preferably both methyl groups or alkyl groups with 2-7 carbon atoms, more preferably both are methyl groups.

In any of the above technical solutions, said polyethylene glycol diether is preferably, for example, at least one of pentaethylene glycol dimethyl ether, hexaethylene glycol dimethyl ether, heptaethylene glycol dimethyl ether, octaethylene glycol dimethyl ether, nonaethylene glycol dimethyl ether and the like.

In any of the above technical solutions, said solvent II is selected from at least one of ethanol, n-propanol, isopropanol, n-butanol, tert-butanol, and isobutyl alcohol.

In any of the above technical solutions, solvent II has a higher dissolving capacity for a part of small molecule impurities such as water and glycolic acid, but has a limited dissolving capacity for another part of impurities glycolic acid oligomer (having a molecular weight of lower than 500 g/mol), polyglycolic acid (having a molecular weight of higher than 500 g/mol). In order to better remove the latter two acidic impurities, solvent I is added to solvent A, because solvent I has a good dissolving capacity for the latter two impurities. In refining step (2), the vast majority of glycolide is present in the solid-liquid mixture in solid form, and a small part of glycolide is dissolved in the solvent, and enters the filtrate together with various impurities dissolved in the solvent during filtering. The filter cake is the glycolide that has been refined in step (1), and various impurities have been significantly reduced, which relieves the burden of cooling crystallization in step (2).

In any of the above technical solutions, said solvent B is selected from at least one of ethanol, n-propanol, isopropanol, n-butanol, tert-butanol, isobutyl alcohol.

In any of the above technical solutions, the crude glycolide is obtained by depolymerization of polyglycolic acid and/or polyglycolic ester, for example, the crude glycolide can be obtained by polycondensation-depolymerization of glycolic acid (ester), or obtained by depolymerization of waste products of polyglycolic acid (PGA), preferably the purity of glycolide therein is greater than or equal to 75 wt % and less than 95 wt %.

In any of the above technical solutions, the purity of the crude glycolide is measured by gas chromatography (GC), and the impurities in the crude glycolide are mainly water, glycolic acid, glycolic acid oligomers (having a molecular weight of lower than 500 g/mol), polyglycolic acid (having a molecular weight of higher than 500 g/mol), glycolic acid oligomers and polyglycolic acid in these impurities are easily soluble in solvent I, and these impurities are separated from glycolide during the filtering process of the solid-liquid mixture in step (1); small molecules such as water and glycolic acid are similar in polarity to solvent II and therefore dissolved in solvent A, and do not separate out solids during cooling and crystallization, and can be separated from glycolide by the filtering operation in steps (1) and (2).

In any of the above technical solutions, the crude glycolide and solvent A in step (1) are mixed and stirred at a constant temperature of 0-40° C., and the preferred constant temperature range is 0-20° C. If the washing temperature is higher than 40° C., the glycolide dissolved in the mixed solvent A will cause obvious loss of refining yield; if the washing temperature is too low, the effect of extracting impurities with solvent A is not ideal.

In any of the above technical solutions, the mass ratio of said crude glycolide and solvent A in step (1) is (0.5-5):1, preferably (0.5-2):1, if the mass ratio is higher, the washing effect will decrease, if the mass ratio is lower, the glycolide dissolved in solvent A can cause an unacceptable loss of refining yield.

In any of the above technical solutions, the filter cake obtained by filtering the solid-liquid mixture in step (1) should have a moisture content as low as possible, in order to minimize solvent I with a higher boiling point remained in the filter cake. The preferred moisture content is less than or equal to 10%, and more preferably less than or equal to 5%.

The filtering operation in step (1) can be carried out in a nitrogen pressure-filtration device, a plate-frame pressure-filtration device, or a centrifugal pressure-filtration device, preferably in a plate-frame pressure-filtration device, or a centrifugal pressure-filtration device, and more preferably in a plate-frame pressure-filtration device.

In any of the above technical solutions, the solvent in the filtrate obtained by filtering the solid-liquid mixture in step (1) is easy to recover. Considering the large difference in boiling points between solvent I and solvent II, solvent I and solvent II can be efficiently separated by fractionation; solvent II is a light component in the fractionation, which is first distilled off and collected, and can be reused in any step of the refining after an optional rectification and a necessary dehydration. Preferably, in the step (1), heavy components remained after the light component is distilled off in the fractionation is homogeneous and transparent with good fluidity, and when placed at 4° C., no solid separates out, indicating that solvent I has a high dissolving capacity for acidic impurities; the above heavy components can be extracted with an organic solvent such as cyclohexane, so that solvent I is forced into the liquid phase, and can be reused in step (1) after the solid-liquid separation and the fractionation.

In any of the above technical solutions, the constant temperature in step (2) does not exceed the boiling point of solvent B, preferably at least 3° C. lower than the boiling point, and the complete dissolution of the glycolide component in the filter cake in step (1) should be ensured. The temperature to which the substance is heated is preferably 70-80° C., more preferably 75-80° C.

In any of the above technical solutions, in step (2), the mass ratio of the filter cake to solvent B is (0.05-5):1, preferably (0.1-1):1.

In any of the above technical solutions, the temperature end point of the cooling crystallization in step (2) is 0-25° C., preferably 15-25° C. In the preferred temperature range, the solubility of glycolide in solvent B is quite low, and the vast majority of glycolide has already crystallized and separated out in this temperature range. Further lowering the end point of the cooling crystallization temperature beyond the preferred temperature range will increase the use load of low-temperature water and increase the energy consumption of the process, but the crystallization yield of glycolide cannot be obviously improved.

In any of the above technical solutions, when the glycolide crystals are collected by filtering after cooling and crystallizing in step (2), the pore size of the filter screen should be less than or equal to 200 microns to reduce the loss of crystals during filtering, and the pore size of the filter screen should be greater than or equal to 50 microns to facilitate the separation of other granular impurities through the filter screen from glycolide.

The filter cake obtained by filtering in step (2) should have a moisture content as low as possible, and the preferred moisture content is less than or equal to 10%, more preferably less than or equal to 5%; the filtering operation can be carried out in a nitrogen pressure-filtration device, a plate-frame pressure-filtration device, or a centrifugal pressure-filtration device, preferably in a plate-frame pressure-filtration device, or a centrifugal pressure-filtration device, and more preferably in a plate-frame pressure-filtration device.

In any of the above technical solutions, the cooling rate after the formation of the glycolide crystal nucleus during cooling and crystallization in step (2) is 5-10° C./hour, the stirring mode after the formation of the crystal nucleus is the intermittent stirring, and the rotation speed does not exceed 20 rpm. The lower cooling rate is for the full and uniform growth of crystals, and the use of the low rotation speed and the intermittent stirring is to ensure the uniform heat transfer during the material cooling.

In any of the above technical solutions, the drying temperature under vacuum does not exceed 40° C., and the preferred drying temperature is 20-30° C. Within the preferred drying temperature range, the glycolide crystals are preferably in a flow state state during vacuum drying. Therefore, the vacuum drying is preferably carried out in a double cone rotary vacuum drier.

The second object of the present invention is to provide the refined glycolide obtained by the process.

The terminal carboxyl content of the refined glycolide obtained in the present invention is 1-10 μmol/g, preferably 2-5 μmol/g.

The technical solution of the present invention introduces polyalkylene glycol ether into the wash of crude glycolide in the saturated monohydric alcohol, so that the acidic impurities (having a molecular weight of about 500 g/mol) in the crude glycolide are fully extracted by the washing solvent, reducing the refining burden of the subsequent recrystallization step. Compared with the prior art, the obtained refined glycolide has the characteristics of lower terminal carboxyl content. The polyalkylene glycol ether used in the technical solution of the present invention can be miscible with saturated monohydric alcohol in a certain proportion, can be easily separated from glycolide during the solid-liquid separation process of the solvent and glycolide, and does not remain in the final refined product. According to the technical solution of the present invention, the saturated monohydric alcohol is separated from glycolide by drying to obtain the refined glycolide product, and the saturated monohydric alcohol is prone to be fully removed, thereby solving the problem of solvent residue in the refined product.

The existing refined glycolide is usually obtained by recrystallizing crude glycolide in a good solvent such as ethyl acetate for several times, then filtering and drying. Since glycolide has a high affinity at the molecular level with the good solvent, making it difficult to fully remove the solvent in the refined glycolide after drying, resulting in the residual purification solvent in the polymer PGA after the ring-opening polymerization reaction, which affects the biomedical application of PGA in the human body. In the technical solution of the present invention, two types of polar solvents are used for the refining of crude glycolide. It has a good extraction effect on acidic impurities such as glycolic acid oligomers. The solvents are easily fully removed during the solid-liquid separation and the drying process. The problem of solvent residue in the refined product is solved. The technical effect of low free acid content in the product is obtained. The technical solutions of the present invention have the technical advantages of easy solvent recovery and low free acid content in the product.

DETAILED DESCRIPTION

The present invention is specifically described below in conjunction with specific embodiments. It is necessary to point out herein that the following examples/embodiments are only used for the further description of the present invention, and cannot be interpreted as a limitation to the protection scope of the present invention. Those skilled in the art can understand some non-essential improvements and modifications to the present invention made according to the content of the present invention still belong to the protection scope of the present invention.

The raw materials used in the specific examples/embodiments of the present invention are commercially available.

The measuring method for the concentration of the free acid of crude glycolide or glycolide of the present invention is as follows:

The concentration of the free acid in crude glycolide is determined by the acid-base titration. The specific operation is as follows: a crude glycolide sample is added to about 30 mL of dry dimethyl sulfoxide, and after it is dissolved, a few drops of bromophenol blue indicator solution is added thereto, and the solution turns yellow. It is titrated with a dilute solution of benzyl alcohol in sodium hydroxide with a known concentration, and it is judged at the endpoint when the colour of the solution changes from yellow to green. The terminal carboxyl amount in glycolide (unit mol) is calculated by calculating the volume of the sodium hydroxide solution used when reaching the titration end point, and then divide by the mass of the crude glycolide sample to obtain the concentration of the free acid of crude glycolide (unit mol/g).

The measuring method for the purity of crude glycolide of the present invention is as follows:

The purity of crude glycolide is determined by gas chromatography (GC). 200 mg of a glycolide sample to be tested and 40 mg of p-chlorobenzophenone as an internal standard substance are dissolved in 10 mL of acetone, 2 μL of the resulting solution is injected into a gas chromatograph to measure the amount of glycolide; the standard calibration line, which is made beforehand with an glycolide standard sample (at least 5 points between 160-200 mg) and the internal standard substance (40 mg) i.e. p-chlorobenzophenone, is used to obtain the purity of glycolide. The measuring device is Agilent 7890B, the chromatographic column is capillary column HP-5 (30 m×0.32 mm, 0.25 μm), the chromatographic column temperature is 280° C., the inlet temperature is 150° C., and the detector is FID.

The measuring method for the purity of refined glycolide of the present invention is as follows:

The purity of the purified glycolide crystals is analyzed with differential scanning calorimetry (DSC). The used instrument model is TA Discovery, and the temperature of glycolide is raised from 65° C. to 95° C. under the condition of controlling the heating rate of 0.5° C./minute. The software that comes with the instrument is used to analyze the purity of glycolide.

The residual solvent content in the refined glycolide of the present invention is determined by high performance liquid chromatography.

The present invention will be further elaborated with the following examples.

Example 1

Poly-condensation-depolymerization preparation of crude glycolide: 600 g of glycolic acid crystals and 6 g of stannous octoate catalyst were added to a reactor, and then the temperature was raised from room temperature to 90° C. After the solid was completely dissolved, the temperature was raised to 120° C. to start the pre-polymerization under atmospheric pressure. After 2 hours of pre-polymerization, the temperature was raised to 210° C. Until no water was distilled off, the system temperature was maintained and then the system began to be vacuumed. The vacuum degree during this process was controlled at 3 kPa until no water was distilled off, and finally 482 g of glycolic acid oligomer was obtained.

The oligomer was provided to a depolymerization reactor, and the depolymerization system was reacted at a reaction temperature of 290° C., a vacuum degree of 3 kPa, and a stirring speed of 100 rpm to prepare crude glycolide, and the reaction was carried out for 2 hours and then stopped to obtain the first batch of crude glycolide (397 g) having an acid content of 452 μmol/g and a glycolide purity of 89.60%.

Example 2

50 g of crude glycolide obtained in Example 1 was mixed with 40 g of n-butanol (having a water content of not higher than 30 ppm) and 10 g of pentaethylene glycol dimethyl ether, and the solid-liquid mixture was stirred at room temperature for 1 hour. The stirring was stopped, and the mixture was filtered by suction to obtain 46 g of filter cake. The filter cake was mixed with 92 g of n-butanol and the mixture was heated to 80° C. to form a homogeneous solution.

Under the condition of the rotating speed of 100 rpm, the solution was cooled to room temperature at a rate of 10° C./h, and glycolide separated out of the system. The resulting mixture was filtered by suction, and the filter cake was subjected to the above-mentioned cooling, recrystallization and filtration process once. The solid obtained by filtering was vacuum dried at 30° C. for 8 hours to give 37.4 g of white crystal in a total yield of 74.8%. The purity of the refined glycolide measured by DSC was 99.73%. The terminal carboxyl content in the refined glycolide measured by the acid-base titration was 3.2 μmol/g. The residual amount of n-butanol and pentaethylene glycol dimethyl ether in the glycolide measured by the liquid chromatography was 0.025%, wherein the residual amount of n-butanol was 225 ppm.

Example 3

50 g of crude glycolide obtained in Example 1 was mixed with 40 g of n-butanol (having a water content of not higher than 30 ppm) and 10 g of nonaethylene glycol dimethyl ether, and the solid-liquid mixture was stirred at room temperature for 1 hour. The stirring was stopped, and the mixture was filtered by suction to obtain 45 g of filter cake. The filter cake was mixed with 90 g of n-butanol and the mixture was heated to 80° C. to form a homogeneous solution. Under the condition of the rotating speed of 100 rpm, the solution was cooled to room temperature at a rate of 10° C./h, and glycolide separated out of the system. The resulting mixture was filtered by suction, and the filter cake was subjected to the above-mentioned cooling, recrystallization and filtration process once. The solid obtained by filtering was vacuum dried at 30° C. for 8 hours to give 36.9 g of white crystal in a total yield of 73.8%. The purity of the refined glycolide measured by DSC was 99.82%. The terminal carboxyl content in the refined glycolide measured by the acid-base titration was 1.8 μmol/g. The residual amount of n-butanol and nonaethylene glycol dimethyl ether in the glycolide measured by the liquid chromatography was 0.015%, wherein the residual amount of n-butanol was 134 ppm.

Example 4

50 g of crude glycolide obtained in Example 1 was mixed with 40 g of isopropanol (having a water content of not higher than 30 ppm) and 10 g of pentaethylene glycol dimethyl ether, and the solid-liquid mixture was stirred at room temperature for 1 hour. The stirring was stopped, and the mixture was filtered by suction to obtain 44 g of filter cake. The filter cake was mixed with 88 g of isopropanol and the mixture was heated to 78° C. to form a homogeneous solution. Under the condition of the rotating speed of 100 rpm, the solution was cooled to room temperature at a rate of 10° C./h, and glycolide separated out of the system. The resulting mixture was filtered by suction, and the filter cake was subjected to the above-mentioned cooling, recrystallization and filtration process once. The solid obtained by filtering was vacuum dried at 30° C. for 8 hours to give 35.8 g of white crystal in a total yield of 71.6%. The purity of the refined glycolide measured by DSC was 99.83%. The terminal carboxyl content in the refined glycolide measured by the acid-base titration was 2.6 μmol/g. The residual amount of isopropanol and pentaethylene glycol dimethyl ether in the glycolide measured by the liquid chromatography was 0.030%, wherein the residual amount of isopropanol was 290 ppm.

Example 5

50 g of crude glycolide obtained in Example 1 was mixed with 40 g of isopropanol (having a water content of not higher than 30 ppm) and 10 g of nonaethylene glycol dimethyl ether, and the solid-liquid mixture was stirred at room temperature for 1 hour. The stirring was stopped, and the mixture was filtered by suction to obtain 44 g of filter cake. The filter cake was mixed with 88 g of isopropanol and the mixture was heated to 78° C. to form a homogeneous solution. Under the condition of the rotating speed of 100 rpm, the solution was cooled to room temperature at a rate of 10° C./h, and glycolide separated out of the system. The resulting mixture was filtered by suction, and the filter cake was subjected to the above-mentioned cooling, recrystallization and filtration process once. The solid obtained by filtering was vacuum dried at 30° C. for 8 hours to give 35.2 g of white crystal in a total yield of 70.4%. The purity of the refined glycolide measured by DSC was 99.74%. The terminal carboxyl content in the refined glycolide measured by the acid-base titration was 2.8 μmol/g. The residual amount of isopropanol and nonaethylene glycol dimethyl ether in the glycolide measured by the liquid chromatography was 0.035%, wherein the residual amount of isopropanol was 336 ppm.

Example 6

50 g of crude glycolide, obtained with the same preparation process as that of Example 1 and having an acid content of 661 μmol/g and a glycolide purity of 83.70%, was mixed with 30 g of isopropanol (having a water content of not higher than 30 ppm) and 20 g of heptaethylene glycol dimethyl ether, and the solid-liquid mixture was stirred at room temperature for 30 minutes. The stirring was stopped, and the mixture was filtered by suction to obtain 42 g of filter cake. The filter cake was mixed with 210 g of isopropanol and the mixture was heated to 78° C. to form a homogeneous solution. Under the condition of the rotating speed of 100 rpm, the solution was cooled to room temperature at a rate of 10° C./h, and glycolide separated out of the system. The resulting mixture was filtered by suction, and the filter cake was subjected to the above-mentioned cooling, recrystallization and filtration process once. The solid obtained by filtering was vacuum dried at 30° C. for 8 hours to give 34.2 g of white crystal in a total yield of 68.4%. The purity of the refined glycolide measured by DSC was 99.78%. The terminal carboxyl content in the refined glycolide measured by the acid-base titration was 3.1 μmol/g. The residual amount of isopropanol and heptaethylene glycol dimethyl ether in the glycolide measured by the liquid chromatography was 0.033%, wherein the residual amount of isopropanol was 318 ppm.

Example 7

50 g of crude glycolide obtained in Example 1 was mixed with 10 g of isopropanol (having a water content of not higher than 30 ppm) and 2.5 g of nonaethylene glycol dimethyl ether, and the solid-liquid mixture was stirred at room temperature for 1 hour. The stirring was stopped, and the mixture was filtered by suction to obtain 46 g of filter cake. The filter cake was mixed with 92 g of isopropanol and the mixture was heated to 78° C. to form a homogeneous solution. Under the condition of the rotating speed of 100 rpm, the solution was cooled to room temperature at a rate of 10° C./h, and glycolide separated out of the system. The resulting mixture was filtered by suction, and the filter cake was subjected to the above-mentioned cooling, recrystallization and filtration process once. The solid obtained by filtering was vacuum dried at 30° C. for 8 hours to give 35.4 g of white crystal in a total yield of 70.8%. The purity of the refined glycolide measured by DSC was 99.58%. The terminal carboxyl content in the refined glycolide measured by the acid-base titration was 5.8 μmol/g. The residual amount of isopropanol and nonaethylene glycol dimethyl ether in the glycolide measured by the liquid chromatography was 0.015%, wherein the residual amount of isopropanol was 142 ppm.

Comparative Example 1

50 g of crude glycolide obtained in Example 1 was recrystallized with 50 mL of ethyl acetate (having a water content of not higher than 30 ppm). The mixture was heated to 70° C. to obtain a solution, then the resulting solution was filtered while hot, and the resulting filtrate was left to cool to room temperature. The solid-liquid mixture, out of which crystals separated, was filtered and dried, and the recrystallization process was repeated once. The obtained solid was vacuum-dried at 30° C. for 8 hours to obtain 30.4 g of white crystals in a total yield of 60.8%. The purity of the refined glycolide measured by DSC was 99.20%. The terminal carboxyl content in the refined glycolide measured by the acid-base titration was 10.1 μmol/g.

The residual amount of ethyl acetate in the glycolide measured by the liquid chromatography was 0.090%.

Comparative Example 2

30.4 g of the refined glycolide obtained in Comparative Example 1 was subjected to the repeated recrystallization process once, and the obtained solid was vacuum-dried at 30° C. for 8 hours to produce 26.5 g of white crystals. The purity of the refined glycolide measured by DSC was 99.7%. The terminal carboxyl content in the refined glycolide measured by the acid-base titration was 2.3 μmol/g. The residual amount of ethyl acetate in the glycolide measured by the liquid chromatography was 0.080%.

Comparative Example 3

50 g of crude glycolide obtained in Example 1 was mixed with 50 g of pentaethylene glycol dimethyl ether, and the solid-liquid mixture was stirred at room temperature for 1 hour. The stirring was stopped, and the mixture was filtered by suction to obtain 38 g of filter cake. The filter cake was mixed with 76 g of pentaethylene glycol dimethyl ether and the mixture was heated to 80° C. to form a homogeneous solution. Under the condition of the rotating speed of 100 rpm, the solution was cooled to room temperature at a rate of 10° C./h, and glycolide separated out of the system. The resulting mixture was filtered by suction, and the filter cake was subjected to the above-mentioned cooling, recrystallization and filtration process once. The solid obtained by filtering was vacuum dried at 30° C. for 8 hours to give 27.2 g of white crystal in a total yield of 54.4%. The purity of the refined glycolide measured by DSC was 99.21%. The terminal carboxyl content in the refined glycolide measured by the acid-base titration was 8.5 μmol/g. The residual amount of pentaethylene glycol dimethyl ether in the glycolide measured by the liquid chromatography was 0.86%.

Comparative Example 4

50 g of crude glycolide obtained in Example 1 was mixed with 50 g of n-butanol (having a water content of not higher than 30 ppm), and the solid-liquid mixture was stirred at room temperature for 1 hour. The stirring was stopped, and the mixture was filtered by suction to obtain 40 g of filter cake. The filter cake was mixed with 80 g of n-butanol and the mixture was heated to 80° C. to form a homogeneous solution. Under the condition of the rotating speed of 100 rpm, the solution was cooled to room temperature at a rate of 10° C./h, and glycolide separated out of the system. The resulting mixture was filtered by suction, and the filter cake was subjected to the above-mentioned cooling, recrystallization and filtration process once. The solid obtained by filtering was vacuum dried at 30° C. for 8 hours to give 28.3 g of white crystal in a total yield of 56.6%. The purity of the refined glycolide measured by DSC was 99.33%. The terminal carboxyl content in the refined glycolide measured by the acid-base titration was 9.6 μmol/g. The residual amount of n-butanol in the glycolide measured by the liquid chromatography was 200 ppm.

Comparative Example 5

50 g of crude glycolide obtained in Example 1 was mixed with 10 g of n-butanol (having a water content of not higher than 30 ppm) and 40 g of nonaethylene glycol dimethyl ether, and the solid-liquid mixture was stirred at room temperature for 1 hour. The stirring was stopped, and the mixture was filtered by suction to obtain 37 g of filter cake. The filter cake was mixed with 74 g of n-butanol and the mixture was heated to 80° C. to form a homogeneous solution. Under the condition of the rotating speed of 100 rpm, the solution was cooled to room temperature at a rate of 10° C./h, and glycolide separated out of the system. The resulting mixture was filtered by suction, and the filter cake was subjected to the above-mentioned cooling, recrystallization and filtration process once. The solid obtained by filtering was vacuum dried at 30° C. for 8 hours to give 27.0 g of white crystal in a total yield of 54.0%. The purity of the refined glycolide measured by DSC was 99.25%. The terminal carboxyl content in the refined glycolide measured by the acid-base titration was 9.1 μmol/g. The residual amount of n-butanol and nonaethylene glycol dimethyl ether in the glycolide measured by the liquid chromatography was 0.098%, wherein the residual amount of n-butanol was 603 ppm.

Example 8

50 g of crude glycolide obtained in Example 1 was mixed with 25 g of n-butanol (having a water content of not higher than 30 ppm) and 25 g of nonaethylene glycol dimethyl ether, and the solid-liquid mixture was stirred at room temperature for 1 hour. The stirring was stopped, and the mixture was filtered by suction to obtain 41 g of filter cake. The filter cake was mixed with 82 g of n-butanol and the mixture was heated to 80° C. to form a homogeneous solution. Under the condition of the rotating speed of 100 rpm, the solution was cooled to room temperature at a rate of 10° C./h, and glycolide separated out of the system. The resulting mixture was filtered by suction, and the filter cake was subjected to the above-mentioned cooling, recrystallization and filtration process once. The solid obtained by filtering was vacuum dried at 30° C. for 8 hours to give 32.1 g of white crystal in a total yield of 64.2%. The purity of the refined glycolide measured by DSC was 99.50%. The terminal carboxyl content in the refined glycolide measured by the acid-base titration was 6.2 μmol/g. The residual amount of n-butanol and nonaethylene glycol dimethyl ether in the glycolide measured by the liquid chromatography was 0.079%, wherein the residual amount of n-butanol was 596 ppm.

In addition, the present invention also provides the following group of technical solutions, specifically including technical solutions A1-A8:

A1. A process for refining glycolide, which comprises a step of extracting impurities from a crude glycolide with solvent A, and then a step of recrystallizing with solvent B, wherein solvent A includes at least two solvents and the solvents are miscible each other;

preferably: said solvent A is a mixed solvent of solvent I and solvent II, solvent I is selected from polyalcohol ethers having the boiling point under atmospheric pressure of greater than or equal to 180° C., solvent I is preferably selected from at least one of polyalkylene glycol ethers, solvent II is selected from saturated alcohols having the boiling point under atmospheric pressure of less than or equal to 120° C., solvent II is preferably selected from at least one of saturated monohydric alcohols;

said solvent B is selected from saturated alcohols having the boiling point under atmospheric pressure of less than or equal to 120° C., preferably selected from at least one of saturated monohydric alcohols; said solvent B is identical to or different from solvent II.

A2. The process for refining glycolide according to technical solution A1, which is characterized in that said process comprises the following steps:

(1) mixing and stirring a crude glycolide and solvent A, then filtering the resulting solid-liquid mixture, and collecting the resulting filter cake;

(2) mixing the filter cake obtained in step (1) with solvent B, heating the resulting mixture, then cooling the resulting solution so as to separate out glycolide crystals, and collecting the resulting filter cake by filtering;

preferably, vacuum drying the obtained filter cake after repeating the step (2) at least once.

A3. The process for refining glycolide according to technical solution A1, which is characterized in that:

in step (1), the mass ratio of the crude glycolide to solvent A is (0.5-5):1, preferably (0.5-2):1; and/or, in step (2), the mass ratio of the filter cake to solvent B is (0.05-5):1, preferably (0.1-1):1.

A4. The process for refining glycolide according to technical solution A1, which is characterized in that:

the mass fraction of solvent II in said solvent A is greater than or equal to 50%, but not equal to 100%, preferably the mass fraction of solvent II is 50-80%.

A5. The process for refining glycolide according to technical solution A1, which is characterized in that:

said solvent I is selected from at least one of polyalkylene glycol monoethers or polyalkylene glycol diethers, preferably selected from polyethylene glycol ethers, more preferably polyethylene glycol diether; and/or, said solvent II is selected from at least one of ethanol, n-propanol, isopropanol, n-butanol, tert-butanol, isobutyl alcohol; and/or, said solvent B is selected from at least one of ethanol, n-propanol, isopropanol, n-butanol, tert-butanol, isobutyl alcohol.

A6. The process for refining glycolide according to technical solution A5, which is characterized in that:

the polymerization degree of ethylene glycol in the polyethylene glycol diether is less than or equal to 20, preferably less than or equal to 10.

A7. The process for refining glycolide according to technical solution A2, which is characterized in that:

in step (1), the temperature for mixing is 0-40° C., preferably 0-20° C.; and/or, in step (2), the temperature to which the resulting mixture is heated is 70-80° C., preferably 75-80° C.; the temperature to which the resulting solution is cooled is 0-25° C., preferably 15-25° C.

A8. The process for refining glycolide according to technical solution A1 or A2, which is characterized in that:

the crude glycolide is obtained by depolymerization of polyglycolic acid and/or polyglycolic ester, and preferably has the glycolide purity of greater than or equal to 75 wt % and less than 95 wt %.

A9. A refined glycolide obtained with the process according to any one of technical solutions A1-A8.

In addition, the present invention also provides the following group of technical solutions, specifically including technical solutions B1-B19:

B1. A process for refining glycolide, comprising the following steps:

(1) a step of extracting impurities from a crude glycolide with solvent A to obtain a glycolide-containing phase and an impurity-containing phase (the glycolide-containing phase refers to a phase in which the content of glycolide is higher than the content of glycolide in the crude glycolide; the impurity-containing phase refers to a phase in which the content of impurities is higher than the content of impurities in the crude glycolide; and the impurities refer to the general term for substances other than glycolide in the crude glycolide);

(2) a step of recrystallizing the glycolide-containing phase with solvent B, wherein solvent A includes at least two solvents and the solvents are miscible each other.

B2. The process for refining glycolide according to any of the aforementioned technical solutions, which is characterized in that said solvent A comprises solvent I and solvent II, solvent I is selected from polyalcohol ethers having the boiling point under atmospheric pressure of greater than or equal to 180° C., solvent II is selected from saturated alcohols having the boiling point under atmospheric pressure of less than or equal to 120° C.

B3. The process for refining glycolide according to any of the aforementioned technical solutions, which is characterized in that in step (1), solvent I and solvent II are added simultaneously or successively.

B4. The process for refining glycolide according to any of the aforementioned technical solutions, which is characterized in that in that step (2) is directly carried out after step (1); or after step (1), the glycolide-containing phase is treated without changing the composition of the glycolide-containing phase, and then step (2) is carried out.

In the present invention, there is no particular limitation on the treatment described in the technical solution B4 as long as the composition of the glycolide-containing phase is not changed. For example, the treatment includes heating, cooling, pressurizing, depressurizing, and storing by standing.

B5. The process for refining glycolide according to any of the aforementioned technical solutions, which is characterized in that said solvent A is a mixed solvent of solvent I and solvent II, solvent I is selected from polyalcohol ethers having the boiling point under atmospheric pressure of greater than or equal to 180° C., solvent II is selected from saturated alcohols having the boiling point under atmospheric pressure of less than or equal to 120° C.

B6. The process for refining glycolide according to any of the aforementioned technical solutions, which is characterized in that said solvent B comprises saturated alcohols having the boiling point under atmospheric pressure of less than or equal to 120° C.; said solvent B is identical to or different from solvent II.

B7. The process for refining glycolide according to any of the aforementioned technical solutions, which is characterized in that said solvent B is a saturated alcohol having the boiling point under atmospheric pressure of less than or equal to 120° C.; said solvent B is identical to or different from solvent II.

B8. The process for refining glycolide according to any of the aforementioned technical solutions, which is characterized in that said solvent A is a mixed solvent of solvent I and solvent II, solvent I is at least one of polyalkylene glycol ethers having the boiling point under atmospheric pressure of greater than or equal to 180° C., solvent II is at least one of saturated monohydric alcohols having the boiling point under atmospheric pressure of less than or equal to 120° C., said solvent B is at least one of saturated monohydric alcohols having the boiling point under atmospheric pressure of less than or equal to 120° C.; said solvent B is identical to or different from solvent II.

B9. The process for refining glycolide according to any of the aforementioned technical solutions, which is characterized in that said process comprises the following steps:

(1) mixing and stirring a crude glycolide and solvent A, then filtering the resulting solid-liquid mixture, and collecting the resulting filter cake;

(2) mixing the filter cake obtained in step (1) with solvent B, heating the resulting mixture, then cooling the resulting solution so as to separate out glycolide crystals, and collecting the resulting filter cake by filtering;

preferably, vacuum drying the obtained filter cake after repeating the step (2) at least once.

B10. The process for refining glycolide according to any of the aforementioned technical solutions, which is characterized in that:

in step (1), the mass ratio of the crude glycolide to solvent A is (0.5-5):1, for example (0.5-2):1; and/or, in step (2), the mass ratio of the filter cake to solvent B is (0.05-5):1, for example (0.1-1):1.

B11. The process for refining glycolide according to any of the aforementioned technical solutions, which is characterized in that:

the mass fraction of solvent II in said solvent A is greater than or equal to 50%, but not equal to 100%, for example, the mass fraction of solvent II is 50-99%, or 50-80%, for example 50%, 60%, 70%, 80%, or 90%.

B12. The process for refining glycolide according to any of the aforementioned technical solutions, which is characterized in that:

said solvent I is selected from at least one of polyalkylene glycol monoethers or polyalkylene glycol diethers, for example polyethylene glycol ethers, e.g. polyethylene glycol diether; and/or, said solvent II is selected from at least one of ethanol, n-propanol, isopropanol, n-butanol, tert-butanol, isobutanol, sec-butyl alcohol, 2-pentanol, 3-pentanol, 2-methyl-2-butanol, 3-methyl-2-butanol; and/or, said solvent B is selected from at least one of ethanol, n-propanol, isopropanol, n-butanol, tert-butanol, isobutanol, sec-butyl alcohol, 2-pentanol, 3-pentanol, 2-methyl-2-butanol, 3-methyl-2-butanol.

B13. The process for refining glycolide according to technical solution B12, which is characterized in that:

the polymerization degree of ethylene glycol in the polyethylene glycol diether is less than or equal to 20, for example, less than or equal to 10.

B14. The process for refining glycolide according to technical solution B9, which is characterized in that:

in step (1), the temperature for mixing is 0-40° C., for example 0-20° C.; and/or, in step (2), the temperature to which the resulting mixture is heated is 70-80° C., for example 75-80° C.; the temperature to which the resulting solution is cooled is 0-25° C., for example 15-25° C.

B15. The process for refining glycolide according to any of the aforementioned technical solutions, which is characterized in that:

the crude glycolide is obtained by depolymerization of polyglycolic acid and/or polyglycolic ester, and for example has the glycolide purity of greater than or equal to 75 wt % and less than 95 wt %.

B16. The process for refining glycolide according to any of the aforementioned technical solutions, wherein said crude glycolide is in a solid or molten state, preferably, the crude glycolide has the terminal carboxyl content of greater than 10 μmol/g, preferably greater than 100 μmol/g, more preferably greater than 500 μmol/g.

B17. A refined glycolide obtained with the process according to any one of technical solutions B1-B16, preferably, the refined glycolide contains (a) a polyalcohol ether having the boiling point under atmospheric pressure of greater than or equal to 180° C. such as a polyalkylene glycol ether having the boiling point under atmospheric pressure of greater than or equal to 180° C., and (b) a saturated alcohol having the boiling point under atmospheric pressure of less than or equal to 120° C. such as a saturated monohydric alcohol having the boiling point under atmospheric pressure of less than or equal to 120° C., wherein, based on the total weight of the refined glycolide, the contents of component (a) and component (b) are greater than or equal to zero, preferably both greater than zero, and the total content of component (a) and component (b) is not greater than 800 ppm, preferably not greater than 500 ppm, preferably, the content of component (a) is greater than zero and less than 300 ppm, the content of component (b) is greater than zero and less than 600 ppm, more preferably, the content of component (a) is greater than 5 ppm and less than 200 ppm, the content of component (b) is greater than 100 ppm and less than 600 ppm, still particularly preferably, the content of component (a) is greater than 5 ppm and less than 30 ppm, the content of component (b) is greater than 125 ppm and less than 350 ppm; and/or wherein the terminal carboxyl content of the refined glycolide is 1-10 μmol/g, preferably 2-5 μmol/g.

B18. A glycolide-containing composition, wherein the composition contains glycolide, and (a) a polyalcohol ether having the boiling point under atmospheric pressure of greater than or equal to 180° C. such as a polyalkylene glycol ether having the boiling point under atmospheric pressure of greater than or equal to 180° C., and (b) a saturated alcohol having the boiling point under atmospheric pressure of less than or equal to 120° C. such as a saturated monohydric alcohol having the boiling point under atmospheric pressure of less than or equal to 120° C., wherein, based on the total weight of the glycolide-containing composition, the contents of component (a) and component (b) are greater than or equal to zero, preferably both greater than zero, and the total content of component (a) and component (b) is not greater than 800 ppm, preferably not greater than 500 ppm, preferably, the content of component (a) is greater than zero and less than 300 ppm, the content of component (b) is greater than zero and less than 600 ppm, more preferably, the content of component (a) is greater than 5 ppm and less than 200 ppm, the content of component (b) is greater than 100 ppm and less than 600 ppm, still particularly preferably, the content of component (a) is greater than 5 ppm and less than 30 ppm, the content of component (b) is greater than 125 ppm and less than 350 ppm; and/or wherein, in the glycolide-containing composition, the terminal carboxyl content is 1-10 μmol/g, preferably 2-5 μmol/g.

B19. A composite solvent, characterized in that the composite solvent consists of:

(a) a polyalcohol ether having the boiling point under atmospheric pressure of greater than or equal to 180° C. such as a polyalkylene glycol ether having the boiling point under atmospheric pressure of greater than or equal to 180° C., and (b) a saturated alcohol having the boiling point under atmospheric pressure of less than or equal to 120° C. such as a saturated monohydric alcohol having the boiling point under atmospheric pressure of less than or equal to 120° C., wherein the weight ratio of component (a) to component (b) is 50:50 to 1:99.

In this disclosure, room temperature means 15-20° C. unless otherwise indicated.

In this disclosure, percentages are by weight unless otherwise indicated.

The invention claimed is:

1. A process for refining glycolide, comprising the following steps:

1) mixing a crude glycolide and solvent A to form a first mixture, filtering the first mixture to obtain a first filter cake and a first filtrate; and 2) mixing the first filter cake with solvent B to form a second mixture, heating the second mixture, then cooling the heated second mixture to form glycolide crystals, filtering the cooled second mixture to obtain a second filter cake and a second filtrate;

wherein solvent A is a mixture of solvent I and solvent II, solvent I is selected from polyalcohol ethers having the boiling point at atmospheric pressure of greater than or equal to 180° C., and solvent II is selected from saturated alcohols having the boiling point at atmospheric pressure of less than or equal to 120° C., and solvent B is selected from saturated alcohols having the boiling point at atmospheric pressure of less than or equal to 120° C.; and solvent B is identical to or different from solvent II.

2. The process for refining glycolide according to claim 1, wherein solvent A is selected from polyalkylene glycol ethers, solvent II is selected from saturated monohydric alcohols, and solvent B is selected from saturated monohydric alcohols.

3. The process for refining glycolide according to claim 1, further comprising vacuum drying the second filter cake.

4. The process for refining glycolide according to claim 1, wherein:

in step 1), a mass ratio of the crude glycolide to solvent A is (0.5-5):1; and/or, in step 2), a mass ratio of the filter cake obtained in step 1) to solvent B is (0.05-5):1.

5. The process for refining glycolide according to claim 1, wherein a mass fraction of solvent II in solvent A is 50-99%.

6. The process for refining glycolide according to claim 1, wherein:

solvent I is selected from at least one of polyalkylene glycol monoethers and polyalkylene glycol diethers; and/or, solvent II is selected from at least one of ethanol, n-propanol, isopropanol, n-butanol, tert-butanol, iso-butanol, sec-butyl alcohol, 2-pentanol, 3-pentanol, 2-methyl-2-butanol, and 3-methyl-2-butanol; and/or, solvent B is selected from at least one of ethanol, n-propanol, isopropanol, n-butanol, tert-butanol, iso-butanol, sec-butyl alcohol, 2-pentanol, 3-pentanol, 2-methyl-2-butanol, and 3-methyl-2-butanol.

7. The process for refining glycolide according to claim 6, wherein solvent I is polyethylene glycol diether having a polymerization degree of ethylene glycol in the polyethylene glycol diether of less than or equal to 20.

8. The process for refining glycolide according to claim 1, wherein:

in step 1), mixing the crude glycolide and solvent A is carried out at 0-40° C.; and/or, in step 2), the second mixture is heated to 70-80° C., and the heated second mixture is cooled to 0-25° C.

9. The process for refining glycolide according to claim 1, wherein the crude glycolide is obtained by depolymerization of polyglycolic acid and/or polyglycolic ester.

10. The process for refining glycolide according to claim 1, wherein the crude glycolide is in a solid or molten state, and has a terminal carboxyl content of greater than 10 μmol/g.

* * * * *